United States Patent [19]

Perlin

[11] 4,210,132
[45] Jul. 1, 1980

[54] ARTIFICIAL SPHINCTER

[75] Inventor: Alfred R. Perlin, Highland Park, Ill.

[73] Assignee: The Kendall Company, Boston, Mass.

[21] Appl. No.: 928,203

[22] Filed: Jul. 26, 1978

[51] Int. Cl.² .................................................. A61B 19/00
[52] U.S. Cl. ...................................... 128/1 R; 128/283;
128/DIG. 25
[58] Field of Search ................ 128/283, DIG. 25; 3/1,
3/1.1; 428/900

[56] References Cited

U.S. PATENT DOCUMENTS

| | | | |
|---|---|---|---|
| 1,810,466 | 6/1931 | Deutsch | 128/348 |
| 2,243,529 | 5/1941 | Grossman et al. | 128/283 |
| 2,324,520 | 7/1943 | Lamson | 128/283 |
| 2,455,859 | 12/1948 | Foley | 128/346 |
| 2,494,393 | 1/1950 | Lamson | 128/1 |
| 2,510,766 | 6/1950 | Surface | 128/1 |
| 2,533,924 | 12/1950 | Foley | 128/346 |
| 2,543,773 | 3/1951 | Goldschmidt | 32/2 |
| 2,564,399 | 8/1951 | Franken | 128/283 |
| 2,638,093 | 5/1953 | Kulick | 128/133 |
| 2,649,086 | 8/1953 | Slutjer | 128/1 R |
| 2,649,854 | 8/1953 | Salm | 128/1 |
| 2,703,576 | 3/1955 | Furr, Jr. | 128/283 |
| 2,792,536 | 5/1957 | Immel | 3/1 |
| 3,066,667 | 12/1962 | Berry | 128/1 |
| 3,080,865 | 3/1963 | Vincent | 128/98 |
| 3,083,704 | 4/1963 | Swearingen | 128/1 |
| 3,147,754 | 9/1964 | Koessler | 128/346 |
| 3,155,096 | 11/1964 | Outwin | 128/346 |
| 3,203,421 | 8/1965 | Bialick | 128/346 |
| 3,216,420 | 11/1965 | Smith et al. | 128/283 |
| 3,253,594 | 5/1966 | Matthews et al. | 128/343 |
| 3,372,695 | 3/1968 | Beliveau et al. | 128/1 |
| 3,384,073 | 5/1968 | Van Winkle, Jr. | 128/1 |
| 3,419,008 | 12/1968 | Plishner | 128/346 |
| 3,447,533 | 6/1969 | Spicer | 128/283 |
| 3,503,400 | 3/1970 | Osthagen et al. | 128/349 |
| 3,538,917 | 11/1967 | Selker | 128/326 |
| 3,554,184 | 1/1971 | Habib | 128/1 |
| 3,565,073 | 2/1971 | Glesy | 128/283 |
| 3,575,158 | 4/1971 | Summers | 128/1 |
| 3,613,661 | 10/1971 | Shah | 128/1 R |
| 3,642,004 | 2/1972 | Osthagen et al. | 128/349 R |
| 3,646,616 | 3/1972 | Keshin | 3/1 |
| 3,646,929 | 3/1972 | Bonnar | 128/1 R |
| 3,650,275 | 3/1972 | Von Der Mozel | 128/407 |
| 3,705,575 | 12/1972 | Edwards | 128/1 R |
| 3,705,580 | 12/1972 | Gauthier | 128/79 |
| 3,730,186 | 5/1973 | Edmunds, Jr. et al. | 128/325 |
| 3,731,670 | 5/1973 | Loe | 128/1 R |
| 3,744,063 | 7/1973 | McWhorter et al. | 3/1 |
| 3,750,194 | 8/1973 | Summers | 3/1 |
| 3,758,073 | 9/1973 | Schutte | 251/342 |
| 3,768,102 | 10/1973 | Kwan-Gett | 3/1 |
| 3,789,828 | 2/1974 | Schutte | 128/1 R |
| 3,797,478 | 3/1974 | Adrian et al. | 128/1 R |
| 3,810,259 | 5/1974 | Summers | 3/1 |
| 3,812,841 | 5/1974 | Issacson | 128/1 R |
| 3,815,576 | 6/1974 | Balabian | 128/1 R |
| 3,815,577 | 6/1974 | Bucalo | 128/1 R |
| 3,817,237 | 6/1974 | Bolduc | 128/1 R |
| 3,841,304 | 10/1974 | Jones | 128/1 R |
| 3,854,469 | 12/1974 | Giori | 128/1 R |
| 3,863,622 | 2/1975 | Buuck | 128/1 R |
| 3,866,611 | 2/1975 | Baumrucker | 128/346 |
| 3,875,928 | 4/1975 | Angerchik | 128/1 R |
| 3,903,894 | 9/1975 | Rosen et al. | 128/346 |
| 3,924,631 | 12/1975 | Mancusi | 128/346 |
| 3,926,175 | 12/1975 | Allen et al. | 128/1 R |
| 3,939,821 | 2/1976 | Roth | 128/1 R |
| 3,952,726 | 4/1976 | Hennig et al. | 128/1 R |
| 4,019,498 | 4/1977 | Hawtrey et al. | 128/1 R |
| 4,019,499 | 4/1977 | Fitzgerald | 128/1 R |
| 4,024,855 | 5/1977 | Bucalo | 128/1 R |
| 4,030,500 | 6/1977 | Ronquist | 128/283 |
| 4,050,461 | 9/1977 | Ruby | 128/227 |
| 4,054,140 | 10/1977 | Etes | 128/283 |

FOREIGN PATENT DOCUMENTS 2717607  10/1978  Fed. Rep. of Germany ... 128/DIG. 25

*Primary Examiner*—John D. Yasko
*Attorney, Agent, or Firm*—Powell L. Sprunger

[57] ABSTRACT

An artificial sphincter for closure of a channel in a patient's body communicating with an opening adjacent the outside of the patient's body. The sphincter comprises, a generally annular member containing a first material for placement around the channel of the patient's body, and a plug having elongated flexible sidewalls of an elastic material for placement within the annular member in the body channel. The plug contains a particulate second material positioned in a region within the annular member when the plug is located in the patient's body. At least one of the first and second materials comprises a permanent magnetic material, while the other of the first and second materials comprises a material substantially susceptible to the one magnetic material. The sphincter has an applicator for selective placement and removal of the plug relative the channel in the patient's body.

36 Claims, 12 Drawing Figures

SKETCH OF MAJOR FORCES ACTING ON PLUG $P < F_a + T + \mu F_p + \mu F_r$

P - INTESTINAL PRESSURE
Fa - AXIAL MAGNETIC FORCE
Fr - RADIAL MAGNETIC FORCE
Fp - RADIAL FORCE DUE TO STRETCHING OF THE BAG
μFp - FRICTION FORCE DUE TO Fp
μFr - FRICTION FORCE DUE TO Fr
T - FORCE DUE TO SHEAR STRESS

ARTIFICIAL SPHINCTER

BACKGROUND OF THE INVENTION

The present invention relates to closure devices, and more particularly to artificial sphincters.

A large number of temporary and permanent ostomy procedures are undertaken by surgeons each year to correct some difficulty in the intestinal tract, such as an obstruction or cancer in the tract. Most commonly, during the procedure the intestine is severed and an end of the intestine is brought through an incision in the abdominal wall. The surgeon then secures the intestine end adjacent the patient's skin, and forms an opening, termed a "stoma", at the juncture of the intestine and skin to permit passage of faecal matter outside the patient's body. In the case of a colostomy procedure, an end of the colon is joined to the skin to form the stoma. In the case of an ileostomy procedure, an end of the ileum is used to form the stoma, resulting in passage of corrosive fluids containing digestive enzymes and acids outside the patient's body.

The ostomy procedure results in loss of faecal continence for the patient, and typically the patient has been required to wear a pouch on the outside of the body in order to collect the faecal matter passing through the stoma. In an attempt to overcome incontinence, many physicians have advised daily irrigation of the intestine by the patient through the stoma. However, the irrigation procedure is very time consuming and inconvenient, and has not alleviated the need for use of stoma bags in many patients, particularly on social occasions. Further, the irrigation procedure may result in ulceration or inadvertent perforation of the intestine. Surgical attempts have also been made to secure continence, such as by formation of a so-called "Kock Pouch", but the procedures have been accompanied by complications.

It has also been proposed to achieve continence with various types of closure devices for the stoma. Such a device should assure adequate closure of the intestine in order to prevent loss of confidence by the patient, particularly in social surroundings, else the patient is required to use a stoma bag which defeats the purpose of the closure device. On the other hand, an adequate seal must be obtained while applying minimal forces against the intestine in order to prevent necrosis. Further, the device should permit simplified placement for patient convenience, and should be light in weight to minimize the possibility of complications resulting from gravitational forces in the region of the stoma and to assure patient comfort.

SUMMARY OF THE INVENTION

A principal feature of the present invention is the provision of an improved artificial sphincter of simplified construction for closure of a channel in a patient's body communicating with an opening adjacent the outside of the patient's body.

The sphincter comprises, a generally annular member containing a first material for placement around the channel of the patient's body. The sphincter has a plug having elongated flexible sidewalls of an elastic material for placement within the annular member in the body channel with the plug sidewalls engaging against walls of the channel in a closure position of the plug. The plug contains a particulate second material positioned in a region within the annular member when the plug is located in the closure position, with at least one of the first and second materials comprising a permanent magnetic material, and the other of the first and second materials comprising a material substantially susceptible to the one magnetic material. The sphincter has applicator means for modifying the engagement force between the plug sidewalls and the walls of the body channel.

A feature of the present invention is that the first and second materials cause engagement of the plug sidewalls against the walls of the body channel in the closure position of the plug.

Thus, a feature of the present invention is that the plug assures adequate closure of the channel in the patient's body.

Another feature of the present invention is that the closure forces acting on the plug are dependent upon the pressure of body fluids in the channel, such that the closure forces are relatively slight when minimal pressure exists in the channel, and the closure forces increase responsive to increased pressure in the channel to insure adequate closure by the plug.

Still another feature of the invention is that the plug applies minimal forces necessary to obtain closure, and minimizes the possibility of necrosis to the channel walls in the patient's body.

Yet another feature of the invention is that the applicator means permits simplified placement and removal of the plug relative the patient's body.

Further features will become more fully apparent in the following description of the embodiments of this invention and from the appended claims.

DESCRIPTION OF THE PREFERRED EMBODIMENTS

Figures 1, 2, 3, 4:
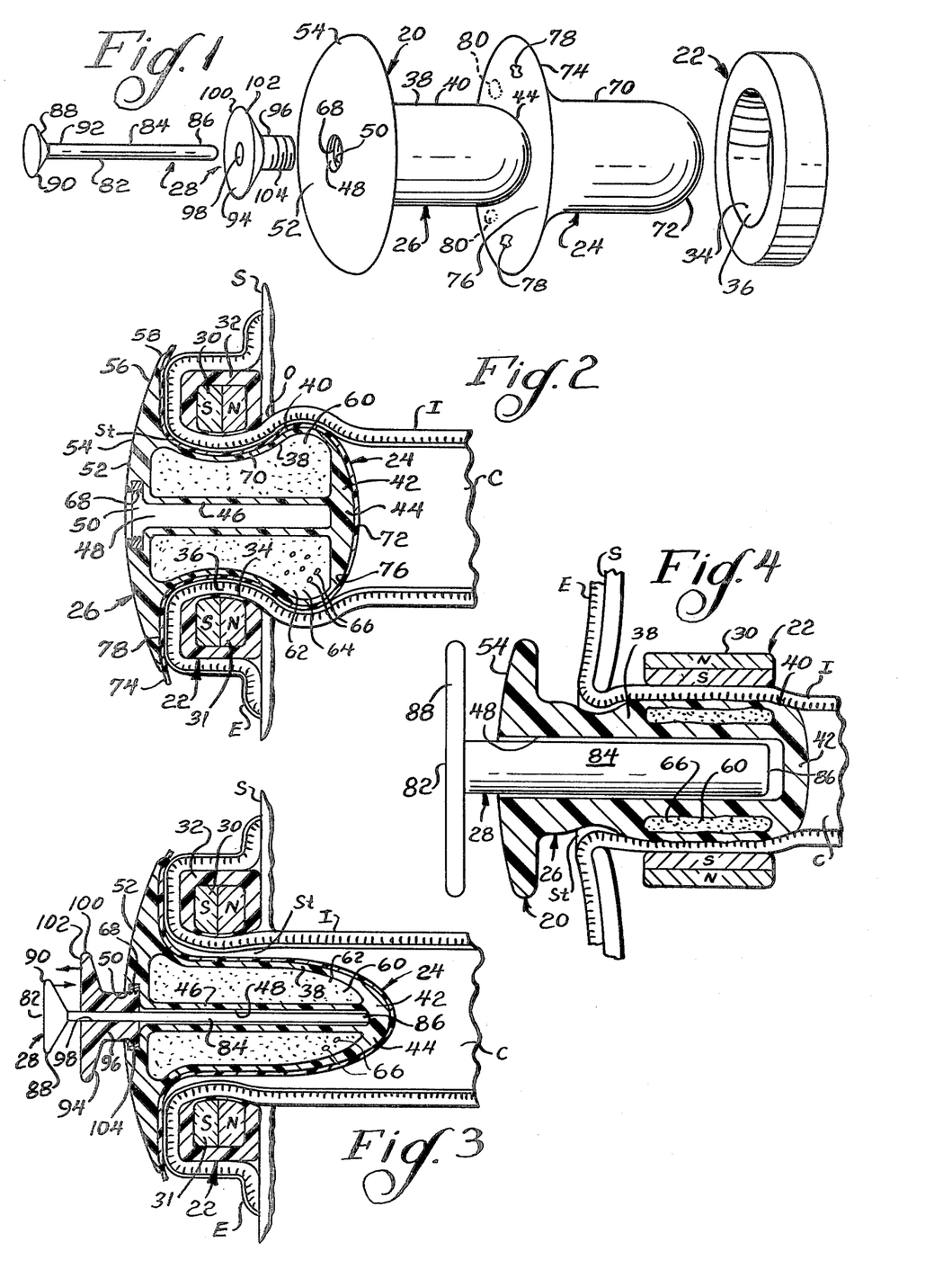
FIG. 1 is an exploded perspective view of an embodiment of an artificial sphincter of the present invention.
FIG. 2 is a sectional view of the sphincter of FIG. 1 illustrating a plug in a closure position in a patient's body.
FIG. 3 is a sectional view of the sphincter of FIG. 1 illustrating use of an applicator to permit placement and removal of the plug.
FIG. 4 is an elevational view, taken partly in section, of another embodiment of an artificial sphincter of the present invention.

Referring now to FIGS. 1 and 2, there is shown an artificial sphincter generally designated 20 for the intestine, including the colon, having an annular member 22, a protective sleeve 24, a plug 26, and an applicator 28. With reference to FIG. 2, the annular member 22 has a ring 30 of a first material 31, and an outer sheet 32 of a biological inert material, such as silicone, covering the outer surface of the ring 30. As shown, during colostomy an outer end E of an intestine I in a patient's body is brought through an opening or incision O adjacent the patient's skin S, with the intestine end E being secured to the patient's skin in order to form a stoma St, and with the annular member 22 being located intermediate the intestine I and the patient's skin S adjacent the intestine end E. With reference to FIGS. 1 and 2, the annular member 22 has a relatively smooth inner surface 34 defining an opening 36 through which the intestine is passed, with the diameter of the opening 36 being approximately equal to the diameter of the intestine adjacent the skin S.

The plug 26 is constructed of an elastic material, such as a suitable plastic, and has an outer annular wall 38 defining an outer surface 40 facing toward the intestine I when the plug is placed in a closure position, and a distal wall 42 extending from the outer wall 38 and closing a distal end 44 of the plug. The plug 26 has an annular inner wall 46 defining an elongated central passageway 48 extending from the distal wall 42 to an opening 50 at a proximal end 52 of the plug 26, and an outwardly directed annular rim 54 which includes an outer flange 56 overlying the annular member 22 and defining an outer edge 58 of the rim 54. As shown, the outer wall 38 and inner wall 46 at least partially define an elongated chamber 60 in the plug having a length greater than the length of the annular member 22. The plug has a suspension 62 in the chamber 60 comprising a liquid 64, such as a viscous oil, and a particulate second material 66 suspended in the liquid 64. The plug 26 also has a threaded portion 68 adjacent a proximal end of the passageway 48 for a purpose which will be described below.

The sleeve 24 may be constructed of any suitable flexible material which is convenient for disposable use, such as a suitable plastic material. The sleeve 24 has an elongated tubular portion 70, a closed distal end 72, and an annular outwardly flared proximal portion 74, with the sleeve 24 defining a cavity 76 to receive the distal portion of the plug 26. Prior to placement of the plug 26 in the intestine, a sleeve 24 may be placed over the plug in order to protect the plug from corrosive fluids and minimize soiling of the plug during use. After removal of the plug from the patient's body, the soiled sleeve 24 may be removed from the plug and may be discarded, after which a new sleeve may be placed on the plug for subsequent use of the device. If desired, the sleeve 24 may have attachment means 78, such as areas of adhesive, for releasably attaching the sleeve proximal portion 74 to the plug flange 56. Also, if desired, the proximal portion 74 of the sleeve 24 may have attachment means 80, such as regions of adhesive, for securement of the sleeve 24 to the intestine I in a releasable manner.

The applicator 28 includes an applicator member 82 having an elongated rod 84 with a length greater than the length of the passageway 48 in the plug 26, such that a distal end 86 of the rod 84 is permitted to engage the distal wall 42 of the plug 26 when the applicator member 82 is positioned in the passageway 48. The applicator member 82 also has a handle 88 in the form of an outwardly directed rim 90 connected to a proximal end 92 of the rod 84.

The applicator 28 also has a retaining member 94 having a tubular section 96 defining a channel 98 to receive the rod 84 of the applicator member 82. The retaining member 94 also has a retaining portion 100 in the form of an outwardly directed rim 102 at the proximal end of the retaining member 94, and a threaded portion 104 at the distal end of the tubular section 96. The threaded portion 104 of the retaining member 94 and the threaded portion 68 of the plug 26 cooperate with each other, such that the distal end of the retaining member 94 may be secured to the proximal end of the plug 26, with the channel 98 of the retaining member 94 aligned with the passageway 48 in the plug 26.

At least one of said first and second materials 31 and 66 comprises a permanent magnetic material, such as a samarium-cobalt magnet, while the other of the first and second materials 31 and 66 comprises a material which is substantially susceptible to the one magnetic material, such as a magnetic material or a ferromagnetic material. With respect to magnetic properties, substances are generally classified as ferromagnetic, paramagnetic, and diamagnetic materials. A permeability $\mu$ is associated with substances, where $\mu = \mu_o$ for a vacuum ($\mu_o/4\pi = 10^{-7}$ Weber/amp-m.), $\mu$ is slightly greater than $\mu_o$ for paramagnetic materials, $\mu$ is slightly smaller than $\mu_o$ for diamagnetic materials, and $\mu$ is often much larger than $\mu_o$ for ferromagnetic materials. Apparently, iron, nickel and cobalt are technically considered the only ferromagnetic materials, but certain alloys display similar properties. Hence, for purposes under discussion, the term "ferromagnetic" will be taken in a broader sense to include materials which display properties akin to the classified ferromagnetic materials.

In a preferred form, the first material 31 in the ring 30 of the annular member 22 comprises a permanent magnetic material, which may be axially magnetized, as shown. Although the second material 66 in the plug chamber may comprise particles of a permanent magnetic material, in a preferred form, the second material 66 comprises a non-magnetized particulate ferromagnetic material, such as iron filings suspended in oil.

In use, a sleeve 24 is placed in protective position over the plug 26, and the retaining member 94 of the applicator 28 is secured to the plug 26 through use of the cooperating threaded portions 104 and 68. Next, the rod 84 of the applicator member 82 is inserted through the channel 98 of the retaining member 94 into the passageway 48 of the plug 26. With reference to FIG. 3, the rim 102 of the retaining member 94 and the rim 90 of the applicator member 82 are squeezed toward each other by the user, such that the distal end 86 of the rod 84 bears upon the distal end 44 of the plug 26 in order to stretch the plug 26 and outer wall 38 in a longitudinal direction. In this configuration, the transverse dimensions of the plug 26 in the region of the outer wall 38 are reduced to a size less than the diameter of a channel C in the intestine I, such that the plug 26 may be inserted through the stoma St into the channel C without significant contact against the walls of the intestine I. After placement of the plug in the intestine channel C, the applicator member 82 may be released, and the susceptibility of the particulate second material 66 in the plug chamber 60 in combination with the elasticity of the plug walls causes the plug to assume a closure position with the outer plug wall 38 slightly engaging against the walls of the intestine I in the region around the annular member 22, as illustrated in FIG. 2. In this configuration, the plug 26 seals the stoma St and closes the channel C in the intestine I. With reference to FIG. 3, the applicator member 82 may be withdrawn from the passageway 48, and the retaining member 94 may be removed from the plug in order to disassemble the applicator 28 from the plug 26 during use of the sphincter by the patient. When it is desired to remove the plug from the patient's body, the retaining member 94 is again attached to the proximal end of the plug 26, and the applicator member 82 may be utilized to stretch the plug in a manner as previously described to withdraw the outer wall 38 of the plug 26 from the walls of the intestine I, and permit removal of the plug with minimal engagement against the walls of the intestine I.

With reference to FIG. 2, when the plug is in the closure position, a distal portion of the plug chamber 60 and outer wall 38 assumes a bulged, contoured configuration around the distal end of the annular member 22 in order to enhance sealing. A diagrammatic illustration of the major forces which act on the plug in the closure position is set forth in FIG. 12. Initially, an axial force Fa acts on the ferromagnetic material in the plug due to interaction of the magnetic ring and the ferromagnetic material, and serves to oppose displacement of the plug otherwise caused by pressure in the channel C of the intestine I. Second, the magnetic ring attracts the ferromagnetic particles toward the surface of the ring resulting in a radial force Fr which tends to distort the outer plug wall around the sides of the magnetic ring to a diameter D which is greater than the internal diameter d of the ring. The radial force Fr thus adds resistance against withdrawal of the plug from the intestine, and increases the friction between the plug wall and the inner surface of the intestine. Further, a radial force Fp due to the elasticity of the plug wall itself acts in a manner as the radial force Fr. As the plug distorts around the distal side of the magnetic ring, the plug also creates a shear force T which obstructs passage of the plug through the rings. Relatively small frictional forces $\mu$ Fr and $\mu$ Fp, associated with the radial forces Fr and Fp, also exist between the plug and intestine wall where $\mu$ designates the coefficient of friction. Under condition of plug closure, the force associated with the pressure P in the intestine channel C is less than the sum of the following forces: $Fa+T+\mu Fp+\mu Fr$.

Figures 10, 11, 12:
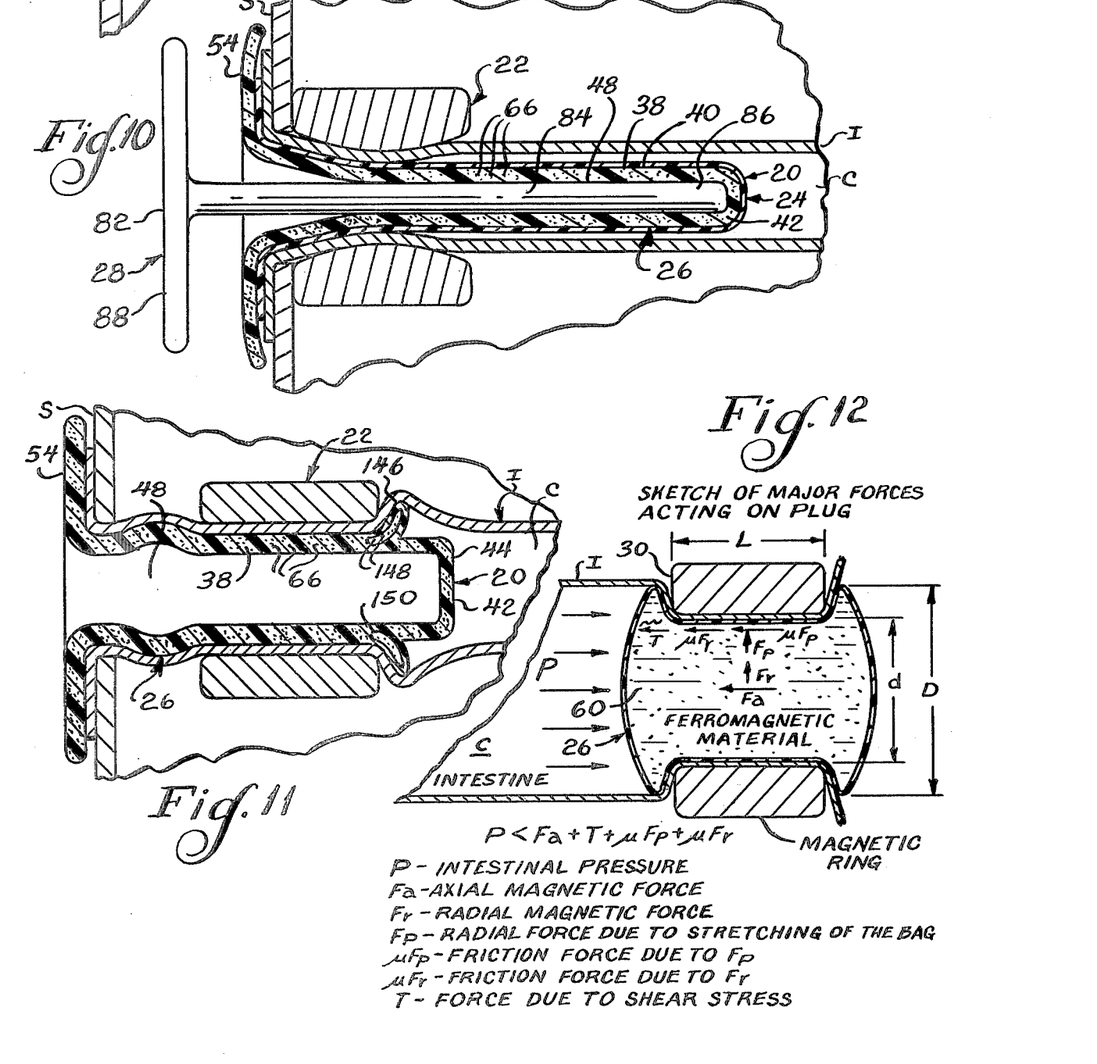
FIG. 10 is an elevational view, taken partly in section, of the sphincter of FIG. 9 illustrating use of an applicator during placement and removal of a plug in the sphincter.
FIG. 11 is a sectional view of another embodiment of an artificial sphincter of the present invention.
FIG. 12 is a diagrammatic view illustrating the configuration of various forces acting during use of the sphincter of the present invention.

The only forces directly acting upon the intestine are the radial forces Fp and Fr and the tangential forces $\mu.Fr$ and $\mu.Fp$, and only part of the total closure force is transmitted to the intestine which is relatively small when the intestine is empty and the pressure P is slight. As the pressure P in the intestine increases subsequent to closure by the plug, the shear force T adjacent the edge of the plug, and to a lesser extent the radial force Fp, increase to enhance the resistance against plug removal responsive to the intestinal pressure. Thus, the plug of the invention acts in a manner minimizing the forces against the intestine required to obtain closure, with the applied forces being particularly slight while minimal pressure exists in the intestine. Further, the plug closure forces automatically increase responsive to increases in intestinal pressure, such that the plug assures proper closure while minimizing forces against the intestine under various pressure conditions in the intestine. In this manner, the plug of the invention provides a seal for the stoma St in the closure position, while minimizing the possibility of pressure necrosis to the intestine.

As previously discussed, the applicator 28 may be utilized to place the plug 26 in the intestine I in order to close the stoma St, and the applicator 28 may also be used to remove the plug 26 from the patient's body when it is desired to empty the intestine I. Thus, in accordance with the present invention, the plug may be readily placed in the closure position, and may be readily removed from the intestine when desired. In addition, the plug of the invention is relatively light in weight, and minimizes the gravitational forces in the region of the stoma St for patient comfort when the plug is in the closure position. Further, the center of gravity of the sphincter lies approximately within the annular member 22, thus preventing possible torque to the annular member within the patient's body.

Another embodiment of the present invention is illustrated in FIG. 4, in which like reference numerals designate like parts. In this embodiment, the outer end E of the intestine I is secured directly to the skin S, and the annular member 22 is placed in a position surrounding the intestine I at a location internal the skin S of the patient's body, although the member 22 may be constructed to extend only partially around the intestine and for convenience has been termed annular. The ring 30 of the annular member 22 may comprise a permanent magnet which may be radially magnetized, as shown. The plug 26 has an annular wall 38 defining an outer surface 40 of the plug and an elongated passageway 48. The plug 26 has a distal wall 42 extending from the annular wall 38 and closing the distal end of the passageway 48. The plug 26 has a circumferential cavity or chamber 60 containing particles of the second material 66, such as iron filings, which are susceptible to or influenced by the magnetic ring 30. The applicator 28 comprises an applicator member 82 having an elongated rod 84, and a handle 88 attached to a proximal end of the rod 84.

During placement, the rod 84 of the applicator 28 is positioned in the passageway 48 of the plug 26, and the handle 88 and a rim 54 at the proximal end of the plug 26 are squeezed toward each other, such that a distal end 86 of the rod 84 bears upon the distal plug wall 42 in order to stretch the plug in a manner as previously described. After insertion of the stretched plug into the channel C of the intestine I, the applicator 28 may be removed from the passageway 48 of the plug 26, such that the outer wall 38 of the plug 26 flexes toward the inner surface of the intestine I due to the affinity between the magnetic ring 30 and the ferromagnetic particles 66 in the plug chamber 60. Thus, the plug 26 automatically assumes a closure position after removal of the applicator 28 from the plug 26. When it is desired to remove the plug 26 from the intestine I, the rod 84 of the applicator member 82 is inserted into the plug passageway 48, and the plug is again stretched with the applicator in order to retract the plug walls from the intestine during removal of the plug.

Figure 5:
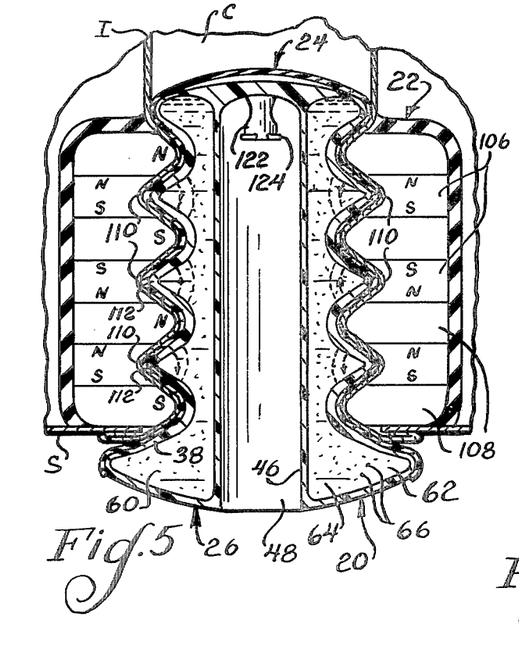
FIG. 5 is a sectional view of another embodiment of an artificial sphincter of the present invention.
Figure 6:
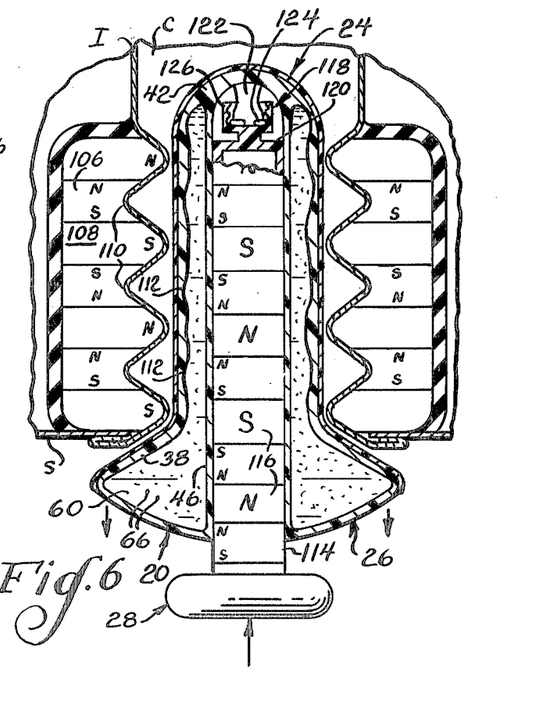
FIG. 6 is an elevational view, taken partly in section, of the sphincter of FIG. 5 illustrating use of an applicator during placement and removal of a plug in the sphincter.

Another embodiment of the present invention is illustrated in FIGS. 5 and 6, in which like reference numerals designate like parts. In this embodiment, the annular member 22 may be placed around the intestine I at a location inside the skin S of the patient. The annular member 22 may comprise a plurality of axially magnetized rings 106 which are spaced by rings 108 of a ferromagnetic or non-ferromagnetic material. In addition, the annular member 22 may define a plurality of circumferential recesses 110 in the region of the magnetic rings 106.

The plug 26 has an annular outer wall 38 and an annular inner wall 46 defining an elongated chamber, with the inner wall 46 defining an elongated passageway 48. As shown, the outer wall 38 may have circumferential regions 112 of reduced thickness and increased flexibility for alignment with the recesses 110 of the annular member. Thus, with reference to FIG. 5, when the plug 26 is in a closure position, the regions 112 of the outer wall 38 flex into the recesses 110 in order to enhance the attachment strength of the plug within the annular member during closure.

With reference to FIG. 6, the applicator 28 may comprise an elongated rod 114 having a plurality of magnets 116 spaced longitudinally along the rod 114. The sphincter 20 may have suitable connection means 118 for releasably attaching a distal end 120 of the applicator rod 114 to the distal wall 42 of the plug 26. The connection means 118 may comprise a post 122 extending proximally from the distal wall 42 of the plug 26, with the post 122 having a proximal outwardly directed flange 124. The rod 114 may have a distal threaded connection member 126 which may be secured on the post flange 124 by rotation of the applicator 28 in a first angular direction, while the connection member 126 may be removed from the post flange 124 through rotation of the applicator 22 in a second reverse angular direction. Thus, the applicator 28 may be readily connected to and removed from the distal wall 42 of the plug 26.

In use, the rod 114 of the applicator 28 is inserted into the passageway 48 of the plug 26, and the connection member 126 of the applicator 28 is attached to the plug post 122 and flange 124. In this configuration, the magnets 116 on the applicator rod 114 attract the ferromagnetic particles in the plug chamber 60 causing the outer plug wall 38 to assume a relatively closely spaced position adjacent the plug inner wall 46. Thus, when the applicator 28 is attached to the plug 26, the transverse dimensions of the plug outer wall 38 become less than the inner dimensions of the intestine I within the annular member 22, such that the plug 26 and the attached applicator 28 may be inserted into the channel C of the intestine I for positioning the plug within the annular member 22. Next, the applicator 28 is rotated in the second angular direction to remove the connection member 126 from the plug post 122, and the applicator 28 is then withdrawn from the passageway 48 of the plug 26. As a result, the particulate material 66 in the plug chamber 60 is attracted toward the magnets in the annular member 22 causing flexation of the plug outer wall 38 toward the intestine I, with the regions 112 of reduced thickness flexing into the circumferential recesses 110 adjacent the magnets. Thus, the plug 26 automatically assumes a closure position after removal of the applicator from the plug 26. When it is desired to remove the plug 26 from the intestine I, the applicator 28 is again inserted into the passageway 48 of the plug 26, and the connection member 126 is attached to the plug post 122 by rotation of the applicator 28 in the first angular direction within the plug. The magnets 116 on the applicator rod 114 are designed to attract the particulate material 66 in the plug chamber 60 with a greater force than the magnets in the annular member 22, such that the outer wall 38 of the plug 26 again assumes a configuration of reduced transverse dimensions adjacent the inner plug wall 46 to permit removal of the applicator 28 and attached plug 26 from the intestine I.

Figure 7:
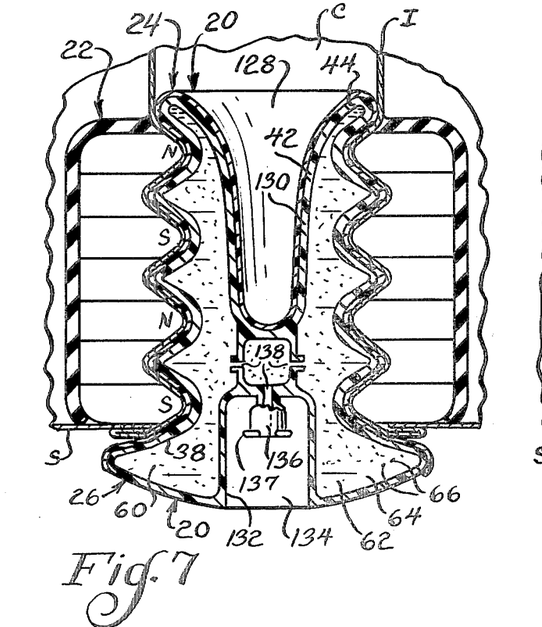
FIG. 7 is a sectional view of another embodiment of an artificial sphincter of the present invention.
Figure 8:
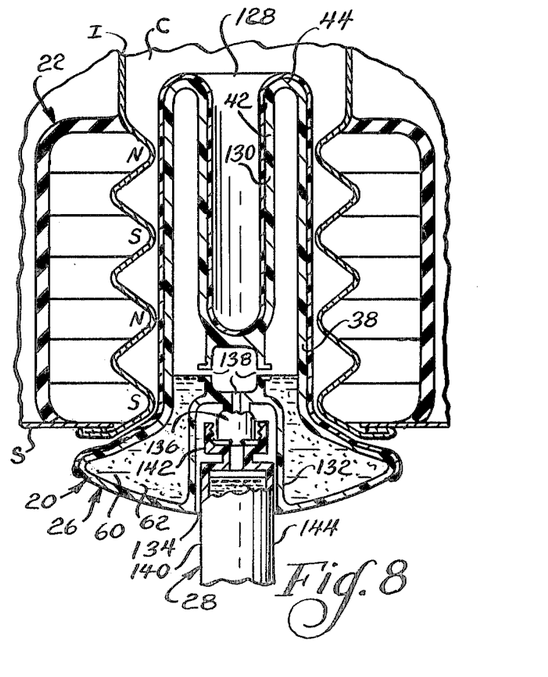
FIG. 8 is a sectional view of the sphincter of FIG. 7 illustrating use of an applicator during placement and removal of a plug in the sphincter.

Another embodiment of the present invention is illustrated in FIGS. 7 and 8, in which like reference numerals designate like parts. In this embodiment, the annular member 22 may be placed around the intestine I at a location within the skin S of the patient, and the annular member 22 may comprise a plurality of annular magnets which may be spaced by suitable rings in a manner as previously described in connection with FIGS. 5 and 6. In this embodiment, the plug 26 has an annular outer wall 38 facing toward the intestine I when the plug is in a closure position. The plug 26 also has a distal wall 42 which defines a central recess 128 extending from a distal end 44 of the plug 26, such that the outer wall 38 and the distal wall 42 form an annular distal portion 130 of the plug walls extending circumferentially around the distal recess 128. Thus, with reference to FIG. 7, when the plug is located in a closure position, the pressure in the channel C of the intestine I as measured in the distal recess 128 biases the plug distal portion 130 toward the annular member 22 in order to enhance the attachment strength and seal of the plug 26 within the annular member 22 responsive to an increase of pressure in the intestine channel C.

As shown in FIG. 7, the plug 26 has a proximal wall 132 defining a passageway 134. The plug 26 also has suitable valve means 136 of known type with a proximal attachment flange 137 positioned within the passageway 134, and a plurality of channels 138 communicating between the valve means 136 and a chamber 60 within the plug 26. With reference to FIG. 8, the applicator 28 comprises a syringe 140 having a distal luer lock 142 which permits releasable attachment of the syringe 140 to the flange 137 of the valve means 136, such that a tip of the attached syringe 140 actuates and opens the valve means 136 in order to permit passage of fluid through the valve means into the plug chamber.

In use, a barrel 144 of the syringe 140 is filled with a suspension comprising a liquid and a suspended second particulate material, such as iron filings. The luer lock 142 of the syringe is attached to the valve means 136 in order to actuate the valve means, and the plug is inserted into the intestine channel C within the annular member 22 while the plug chamber is empty. Next, the syringe 140 is pumped in order to eject the suspension from the syringe through the valve means 136 and plug channels 138 into the chamber 60. As a result, the particulate second material 66 in the plug chamber is attracted toward the magnets in the annular member 22, and the outer wall 38 of the plug 26 flexes against the intestine I within the annular member 22, such that the plug assumes a closure position, as shown in FIG. 7. At this time, the syringe 140 may be removed from the plug to prevent closure of the valve means during use of the sphincter 20. When it is desired to remove the plug 26 from the patient's body, the luer lock 142 of the syringe 140 is again attached to the flange 137 of the valve means 136 in order to actuate the valve means and connect the syringe 140 to the plug 26. Next, with reference to FIG. 8, the suspension 62 may be aspirated from the plug chamber 60 through use of the syringe to permit flexation of the outer plug wall 38 away from the magnets in the annular member 22. Thus, when a substantial portion of the suspension 62 has been removed from the plug chamber 60, the plug 26 becomes disengaged from the intestine I and the plug 26 may be removed from the channel C of the intestine I.

Figure 9:
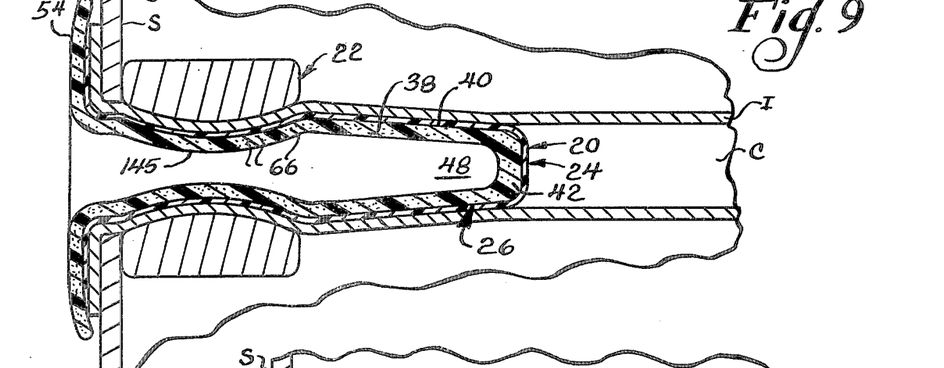
FIG. 9 is a sectional view of another embodiment of an artificial sphincter of the present invention.

Another embodiment of the present invention is illustrated in FIGS. 9 and 10, in which like reference numerals designate like parts. In this embodiment, the annular member 22 again surrounds the intestine I at a location within the skin S of the patient. The plug 26 has an elongated outer wall 38 defining an outer surface 40 facing the inner surface of the intestine I when the plug 26 is in a closure position. The outer wall 38 also defines an elongated passageway 48 which is closed by a distal wall 42 of the plug 26. In this embodiment, the plug 26 has particles of the second material 66 dispersed in the outer wall 38 itself in a region 145 of the wall 38 having a length greater than the length of the annular member 22. In a suitable form, the plug 26 may be molded from a plastic material which contains particles of the second material 66.

With reference to FIG. 10, the applicator 28 comprises an applicator member 82 having an elongated rod 84 and a handle 88 connected to a proximal end of the rod 84. In use, the rod 84 of the applicator 28 is inserted into the passageway 48 of the plug 26, and the distal end 86 of the rod 84 is engaged against the distal wall 42 of the plug 26 in order to stretch the outer wall 38 into a configuration of reduced transverse dimensions. Next, the applicator 28 and stretched plug 26 may be inserted into the channel C of the intestine I, after which the applicator 28 is removed from the plug 26. As a result, the particulate second material 66 in the wall 38 of the plug 26 is attracted toward the magnetic annular member 22 causing flexation of the outer wall 38 into a sealing configuration against the inner surface of the intestine I, such that the plug 26 automatically assumes a closure position within the channel C of the intestine I. When it is desired to remove the plug 26 from the patient's body, the applicator 28 is again inserted into the passageway 48 of the plug in order to stretch the plug outer wall 38 into a configuration of reduced transverse dimensions, as illustrated in FIG. 10, thus permitting simplified removal of the applicator and plug from the channel C of the intestine I.

Another embodiment of the present invention is illustrated in FIG. 11, in which like reference numerals designate like parts. In this embodiment, the annular member 22 may be positioned around the intestine I in a manner as previously described. The plug 26 has an elongated annular outer wall 38 having a particulate second material 66 dispersed in the wall itself as discussed in connection with FIGS. 9 and 10. The plug 26 also has a distal wall 42 closing a distal end of the passageway 48 defined by the outer wall 38.

As shown, the plug 26 has an annular sealing flap 146 adjacent the distal end 44 of the plug 26, with the flap 146 extending outwardly in a direction distally along the plug 26, such that the flap 146 is permitted to flex around the distal side of the annular member 22. In a preferred form, as shown, the sealing flap 146 contains a particulate material 148 which may be of the same type as the second particulate material 66, and, in one form, the particulate material 148 may be retained in an annular cavity 150 within the flap 146.

Thus, when the plug 26 is placed in its closure position within the channel C of the intestine I, the particulate material 148 in the flap 146 causes flexation of the flap 146 toward the distal side of the annular member 22 due to attraction between the particulate material 148 and the magnets in the annular member 22. As the pressure increases in the channel C of the intestine I, the flap 146 is biased with greater force against the distal side of the annular member 22 in order to enhance the seal of the plug 26 in its closure position responsive to intestinal pressure. A suitable applicator of the type previously discussed in connection with FIGS. 4 or 10 may be utilized to place the plug 26 in a closure position within the annular member 22, and to remove the plug 26 from the intestine. Alternatively, an applicator of the type disclosed in connection with FIG. 6 may be utilized for placement and removal of the plug.

The foregoing detailed description is given for clearness of understanding only, and no unnecessary limitations should be understood therefrom, as modifications will be obvious to those skilled in the art.

I claim:

1. An artificial sphincter for closure of a channel in a patient's body communicating with an opening adjacent the outside of the patient's body, comprising:
    a generally annular member containing a first material for placement at least partially around the channel of the patient's body;
    a plug having elongated flexible sidewalls of an elastic material for placement within said annular member in the body channel with the plug sidewalls flexing toward walls of said channel in a closure position of the plug, said plug containing a particulate second material positioned in a region within the annular member when said plug is located in said closure position, at least one of said first and second materials comprising a permanent magnetic material, and the other of said first and second materials comprising a material substantially susceptible to said one magnetic material; and
    applicator means for selectively placing said plug in said closure position and for selectively removing the plug from the body channel comprising means for modifying the transverse dimensions of the plug sidewalls relative to the body channel.

2. The sphincter of claim 1 wherein said annular member extends around an intestine of the patient defining said channel adjacent said opening.

3. The sphincter of claim 1 wherein said annular member is located intermediate an outer end of an intestine and the skin of the patient's body.

4. The sphincter of claim 1 wherein the length of said plug sidewalls is substantially greater than the length of said annular member.

5. The sphincter of claim 1 wherein said first material comprises said one magnetic material.

6. The sphincter of claim 5 wherein said first material is axially magnetized.

7. The sphincter of claim 5 wherein said first material is radially magnetized.

8. The sphincter of claim 5 wherein said first material comprises a plurality of spaced annular magnets.

9. The sphincter of claim 1 including an elongated closed end sleeve of flexible protective material covering said sidewalls and a distal end of said plug.

10. The sphincter of claim 1 wherein said plug sidewalls at least partially define a chamber in the plug, and in which said second particulate material is suspended in a liquid in said chamber.

11. The sphincter of claim 10 wherein said plug includes valve means communicating with said chamber, and in which the applicator means comprises pump means connectable to said valve means for selectively filling the chamber with the liquid and second material, and aspirating the liquid and second material from the chamber.

12. The sphincter of claim 11 wherein the pump means comprises a syringe.

13. The sphincter of claim 1 wherein said second material comprises a magnetic material.

14. The sphincter of claim 1 wherein said second material comprises a ferromagnetic material.

15. The sphincter of claim 1 wherein said plug includes a proximal outwardly directed annular rim for placement over the outside of the patient's body adjacent said opening.

16. The sphincter of claim 1 wherein said plug has an elongated central passageway closed by a distal end of the plug, said passageway communicating with an aperture at a proximal end of the plug.

17. The sphincter of claim 16 wherein the applicator means comprises an elongated magnetized rod for placement in the passageway of the plug.

18. The sphincter of claim 17 including means for releasably attaching a distal end of the rod to the distal end of the plug in said passageway.

19. The sphincter of claim 16 wherein the applicator means comprises an elongated rod having a length greater than the length of said passageway, said rod being received in the passageway with a distal end of the rod bearing against the distal end of the plug to stretch said plug sidewalls away from the walls of the body channel.

20. The sphincter of claim 1 wherein said second material is contained within said plug sidewalls.

21. The sphincter of claim 1 wherein the plug sidewalls include circumferential regions of reduced thickness for increased flexibility in said regions.

22. The sphincter of claim 1 wherein said plug includes a generally annular flexible flap extending in a distal direction adjacent a distal end of the plug, said flap being placed at a location distal the annular member in the body channel in the closure position of the plug.

23. The sphincter of claim 22 wherein at least a portion of said second material is located within said flap.

24. The sphincter of claim 1 wherein said annular member defines a relatively smooth inner surface.

25. The sphincter of claim 1 wherein said annular member defines a plurality of inner circumferential recesses.

26. The sphincter of claim 1 wherein a distal end of the plug has an elongated central recess.

27. An artificial sphincter for closure of a channel in a patient's body communicating with an opening adjacent the outside of the patient's body, comprising:
 a generally annular member containing a first material for placement at least partially around the channel of the patient's body;
 a plug of elastic material having an elongated flexible annular outer wall for facing walls of the body channel, a closed distal end, and an annular inner wall defining an elongated central passageway extending between an opening adjacent a proximal end of the plug and said distal end, said inner and outer walls at least partially defining an elongated chamber in the plug having a length greater than the length of said annular member, said plug containing a fluid and a particulate second material in said chamber, with at least one of said first and second materials comprising a permanent magnetic material, and with the other of said first and second materials comprising a material substantially susceptible to said one magnetic material, said first and second materials causing flexation of said outer wall toward the walls of the body channel in a first closure configuration of the plug; and
 applicator means for selective placement and removal of the plug comprising means for placing the outer wall of the plug in a second configuration with said outer wall in reduced transverse dimensions relative to the walls of said channel.

28. The sphincter of claim 27 wherein said applicator means comprises an applicator member having an elongated rod with a length greater than the length of said passageway, and a handle connected to the rod adjacent a proximal end of the applicator member, with a distal end of the rod bearing upon the distal end of the plug to stretch the plug walls and move the plug from said first configuration to said second configuration during placement and removal of the plug.

29. The sphincter of claim 28 including a retaining member having a channel to receive said rod, a retaining portion adjacent a proximal end of the retaining member, and including means for releasably attaching the retaining member to said plug with the channel of the retaining member aligned with the passageway of the plug, and with said retaining portion located proximal the plug, whereby the rod of the applicator member may be passed through said retaining member channel into said passageway with the retaining member attached to the plug, and the spacing between said handle and retaining portion may be reduced to apply pressure by the distal end of the rod and stretch the plug.

30. The sphincter of claim 29 wherein the attaching means comprises cooperating threads on the distal end of the retaining member and the proximal end of the plug.

31. The sphincter of claim 29 wherein said handle of the applicator member and the retaining portion of the retaining member comprise outwardly directed proximal rims.

32. The sphincter of claim 27 wherein said applicator means comprises an elongated rod for insertion into said passageway, said rod including magnet means to attract said second material in the plug cavity.

33. An artificial sphincter for closure of a channel in a patient's body communicating with an opening adjacent the outside of the patient's body, comprising:
 a generally annular member containing a first material for placement at least partially around the channel of the patient's body;
 a plug of elastic material having a flexible annular outer wall for facing walls of the body channel, a closed distal end, and a chamber with a length greater than the length of said annular member, and valve means communicating with said chamber; and
 pump means for selectively filling the chamber through the valve means with a medium and for selectively withdrawing the medium from the chamber, said medium comprising a liquid and a particulate second material, with at least one of said first and second materials comprising a permanent magnetic material, and with the other of said first and second materials comprising a material substantially susceptible to said one magnetic material.

34. An artificial sphincter for closure of a channel in a patient's body communicating with an opening adjacent the outside of the patient's body, comprising:

a generally annular member containing a first material for placement at least partially around the channel of the patient's body;

a plug of elastic material having an elongated outer wall for facing the walls of the body channel, said outer wall having a length greater than the length of said annular member and defining a central passageway communicating with an opening adjacent a proximal end of the plug, said plug having a distal wall extending from said outer wall and closing a distal end of the passageway, and a particulate second material dispersed in a region of said outer wall having a length greater than the length of said annular member, at least one of said first and second materials comprising a permanent magnetic material, and the other of said first and second materials comprising a material substantially susceptible to said one magnetic material; and applicator means for reducing the transverse dimensions of the outer wall to permit placement and removal of said plug.

35. The sphincter of claim 34 wherein the applicator means comprises an elongated rod receivable in said passageway and having a length greater than the length of the passageway, said rod having a distal end for engaging against said distal wall to stretch the plug during placement and removal.

36. The sphincter of claim 34 wherein the applicator means comprises an elongated rod receivable in the passageway and having magnet means to attract said second material in said outer wall.

* * * * *